(12) United States Patent
Ying

(10) Patent No.: US 9,850,382 B1
(45) Date of Patent: Dec. 26, 2017

(54) UNSYMMETRICAL CYANINE DYES AND THEIR APPLICATION

(71) Applicant: Laiqiang Ying, North Potomac, MD (US)

(72) Inventor: Laiqiang Ying, North Potomac, MD (US)

(73) Assignee: Laiqiang Ying, North Potomac, MD (US)

( * ) Notice: Subject to any disclaimer, the term of this patent is extended or adjusted under 35 U.S.C. 154(b) by 0 days.

(21) Appl. No.: 15/369,867

(22) Filed: Dec. 5, 2016

(51) Int. Cl.
*C09B 23/16* (2006.01)
*C12Q 1/68* (2006.01)

(52) U.S. Cl.
CPC ............. *C09B 23/164* (2013.01); *C12Q 1/68* (2013.01)

(58) Field of Classification Search
CPC .................................................. C09B 23/164
USPC .......................................................... 546/165
See application file for complete search history.

(56) References Cited

U.S. PATENT DOCUMENTS

| | | | |
|---|---|---|---|
| 7,776,529 B2 * | 8/2010 | Dallwig | C07D 277/64 435/6.15 |
| 9,040,561 B2 * | 5/2015 | Dallwig | C07D 277/64 514/314 |

* cited by examiner

Primary Examiner — Taofiq A Solola

(57) ABSTRACT

The invention describes the preparation and use of fluorescent stains for nucleic acids derived from unsymmetrical cyanine dyes. The dyes of the invention possess superior fluorescent properties when complexed with nucleic acids, and have utility in any application which requires detection of nucleic acids, such as detection of nucleic acids in solution, in gels, in blots, in microarrays, and in bacteria and cells, and for use in analysis of cell structure, membrane integrity, and function. The dyes of the invention have the formula

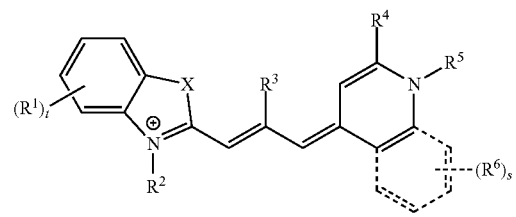

where X is O, S, or $C(CH_3)_2$; Each of $R^1$ and $R^6$ is independently hydrogen, carboxy, sulfo, sulfonamide, halogen, CN, or alkoxy; Each of t and s is an integer from 0 to 4; $R^2$ is an alkyl, or alkyl group substituted by a carboxy, or a sulfo; $R^3$ is H, $C_6H_4CO_2R^7$, or $C_6H_4CH_2N(R^7)_2$, where $R^7$ is an alkyl; $R^4$ is H, alkyl, aryl, halogen, alkoxy, alkylamino, or alkylthio; $R^5$ is an alkyl, aryl, alkyl group substituted by a carboxy, or a sulfo, or $-(CH_2)_a-[O-(CH_2)_b]_m-O-Z$, where Z is H, alkyl, or carboxy; each of a and b is an integer from 1 to 4; m is an integer selected from 0 to 4.

13 Claims, 5 Drawing Sheets

UNSYMMETRICAL CYANINE DYES AND THEIR APPLICATION

CROSS-REFERENCE TO RELATED APPLICATIONS

This application claims the benefit of U.S. Provisional Application No. 62/266,599, filed Dec. 12, 2015, which application is incorporated herein by reference in its entirety.

BACKGROUND

Fluorescent dyes or stains have been widely used in biological detections in which the high detectability of fluorescence is desirable. By binding to a particular target in a biological sample enables researcher to determine the presence or quantity of the target. Nucleic acids, such as DNA and RNA, are involved in the transmission of genetic information from one generation to the next, and the routine functions of live organisms. Nucleic acids are thus of interest and the objects of study. Fluorescent dyes that specifically bind to nucleic acids and form highly fluorescent complexes are useful tools for such study. These dyes can be used for detection of DNA or RNA in a variety of format, including in solution, in electrophoretic gels and blots, in microarray, dead or fixed cells, and live cells.

Several dyes are commercially available for detection of nucleic acids. Unsymmetrical cyanine dyes were described long before much was known about DNA, by Brooker, et al., *J. AM. CHEM. SOC.* 64, 199 (1942). The commercial dye Thiazole Orange has good applications in the quantitative analysis of immature blood cells or reticulocytes. U.S. Pat. No. 4,883,867 to Lee, et al. (1989); Lee, et al., Thiazole Orange: A New Dye for Reticulocyte Analysis, *CYTOMETRY* 7, 508 (1986). But, the limitation of Thiazole Orange is low detection sensitivity on nucleic acids. Ethidium bromide is the most widely used nucleic acid stain, and is commercially available from a number of suppliers. However, ethidium bromide is mutagenic, and its use requires significant care from the user to avoid contact with staining solutions, and special handing and waste disposal procedures (M. J. Waring, *J. Mol. Biol.* I 13, 269 (1965); McCann et al., *Proc. Natl. Acad. Sci. USA,* 72, 5135 (1975); and Fukunaga et al., *Mutation Res.* 127, 31 (19840)). PicoGreen is a stain selective for double stranded DNA and commercially available from Invitrogen; OliGreen is a stain useful for the quantitation of single stranded DNA and commercially available from Invitrogen; RiboGreen is a stain that is useful for quantitation of RNA in solution, and commercially available from Invitrogen; SYBR Green I is a stain selective for DNA and used for DNA gel stains and qPCR quantitation, and commercially available from Invitrogen; SYBR Gold is a high sensitive stain for both DNA and RNA, and commercially available from Invitrogen. These dyes are described in U.S. Pat. Nos. 5,436,134, 5,658,751 and 5,863,753. However, these dyes have low water soluability and have to be predisolved in organic solvent such as DMSO or DMF; and also have limited stability in aqueous solution, and have to be used within 24 hours before losing sensitivity. Another asymmetric cyanine dye, SYBR Safe, is commercially available from Invitrogen as an alternative to SYBR Green I and Ethidium bromide due to its low mutagenicity. This dye is described in U.S. Pat. Nos. 7,727,716 and 7,977,057. However, this alternative dye is less water soluability and low sensitive than desired.

Development of fluorescent dyes with improved water soluability and stability or the making or the use thereof is desirable.

SUMMARY

Methods of designing, producing, or using a fluorescent dye suitable for useful applications, such as in solution detection and quantitation of nucleic acid, or in gel staining of nucleic acids. The dyes used for the invention are non-fluorescent or are minimally fluorescent by themselves, but become highly fluorescent in the presence of nucleic acids. In some embodiments, the dyes used for the invention become highly fluorescent in the presence of DNA or RNA. In some embodiments, the dyes used for the invention have high selectivity for DNA over RNA. In some embodiments, the dyes used for the invention have high selectivity for RNA over DNA.

In some embodiments, the dyes used for the invention are unsymmetric cyanine dyes with a side chain modified by a hydrophilic group to improve water soluability and stability. These dyes may have at least one feature, or all of the following features: relatively low "fluorescence background" (fluorescence in the absence of nucleic acids), if any, and ideally, no fluorescence background; relative low toxicity, and ideally, no toxicity; relatively high fluorescent signal strength; and relative high water soluability and stability in water. These dyes are preferably better as to at least one of these features than existing dyes, such as Ethidium Bromide, SYBR Green I, SYBR Gold, and SYBR Safe. The unsymmetrical cyanine dyes have two aromatic ring groups joined by an unsaturated hydrocarbon chain containing one or more methane groups. The novel dyes generally have the formula:

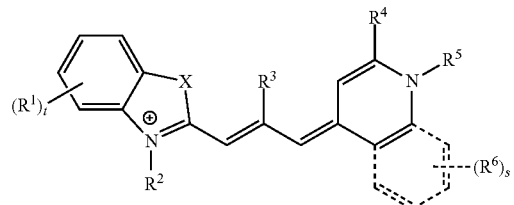

wherein:

X is O, S, or $C(CH_3)_2$;

Each of $R^1$ and $R^6$ is independently hydrogen, carboxy, sulfo, sulfonamide, halogen, CN, or alkoxy;

Each of t and s is an integer from 0 to 4;

$R^2$ is an alkyl, or alkyl group substituted by a carboxy, or a sulfo;

$R^3$ is H, $C_6H_4CO_2R^7$, or $C_6H_4CH_2N(R^7)_2$, where $R^7$ is an alkyl;

$R^4$ is H, alkyl, aryl, halogen, alkoxy, alkylamino, or alkylthio;

$R^5$ is an alkyl, aryl, alkyl group substituted by a carboxy, or a sulfo, or $—(CH_2)_a—[O—(CH_2)_b]_m—O—Z$, where Z is H, alkyl, or carboxy; each of a and b is an integer from 1 to 4; m is an integer selected from 0 to 4.

In some embodiments, a method of detection and quantitation of nucleic acids in a sample is provided. The detection method can be performed in solution, in electrophoretic gels and blots, in microarray, in dead or fixed cells, or in live cells. The method comprises exposing the sample to a fluorescent nucleic acid dye having the formula:

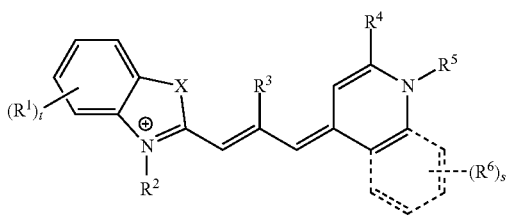

The substitute groups are the same as above-described.

In some embodiments, a kit of detection and quantitation of nucleic acids in a sample is provided. The kit comprises the fluorescent nucleic acid dye just described above, and information concerning use of the fluorescent nucleic acid dye. The kit may comprise, optionally, a buffer, a nucleic acid standard, or gel matrix. The fluorescent nucleic acid dye may be in an organic or aqueous solution, or in a gel matrix, such as a agarose gel matrix, for example.

DETAILED DESCRIPTION

Figure 1:
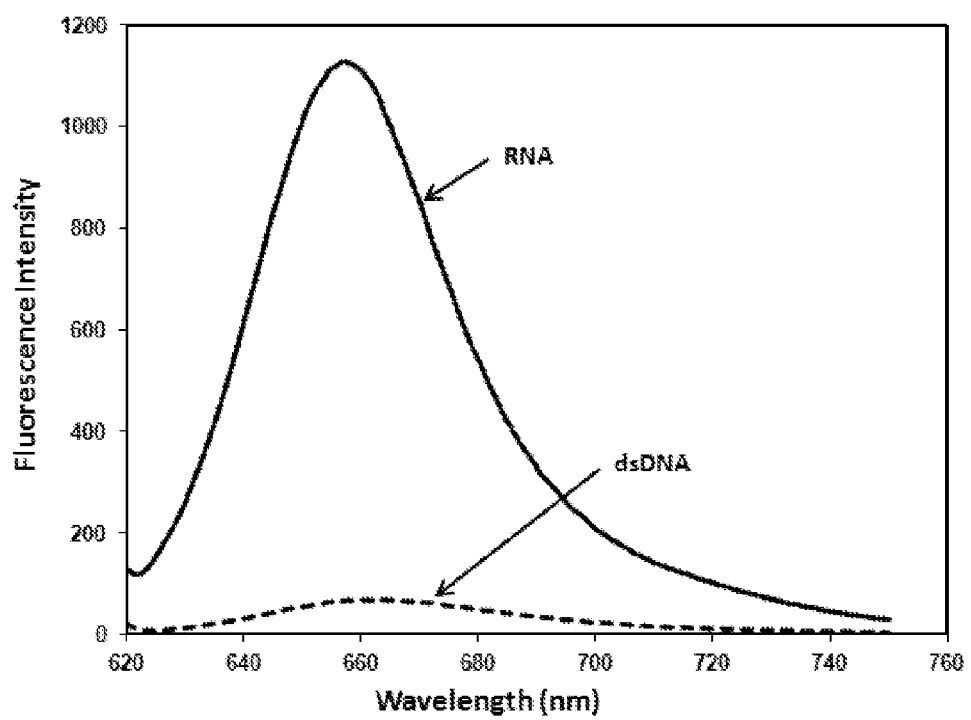
FIG. 1 shows a graphical representation of fluorescence emission spectra of compound 9 in the presence of dsDNA and RNA in TE buffer, respectively.

Fluorescent dyes or stains are useful in various biological applications, such as nucleic acid detection, for example. Methods associated with fluorescent dyes or stains, such as methods of use thereof, for example, are also useful. The unsymmetrical cyanine dyes of the invention are virtually non-fluorescent when diluted in aqueous solution. When bound to nucleic acids, such as DNA or RNA, for example, becomes extremely fluorescent upon illumination. The dyes of the present invention can label nucleic acids in a wide variety of samples, particular in aqueous solutions, electrophoretic gels and blots, microarray, and a wide variety of cells, including microorganisms.

The section headings used herein are for organizational purposes only and are not to be construed as limiting the subject matter described.

Definitions

Unless otherwise defined, scientific and technical terms used in connection with the present invention shall have the meanings that are commonly understood by those of ordinary skill in the art. Further, unless otherwise required by context, singular terms shall include pluralities and plural terms shall include the singular.

In this application, the use of "or" means "and/or" unless stated otherwise. In the context of a multiple dependent claim, the use of "or" refers back to more than one preceding independent or dependent claim in the alternative only.

As utilized in accordance with the present disclosure, the following terms, unless otherwise indicated, shall be understood to have the following meanings:

The terms "stain" and "dye" may be used interchangeably, and refer to an aromatic molecule capable of absorbing light in the spectral range of from about 250 nm to about 1000 nm, inclusive. The term "dye" may refer to a fluorescent dye, a non-fluorescent dye, or both. The term "fluorescent dye" refers to a dye capable of emitting light when excited by another light of appropriate wavelength.

The terms "nucleic acid" refers to double-stranded DNA (dsDNA), single-stranded DNA (ssDNA), double-stranded RNA (dsRNA), single-stranded RNA (ssRNA), and/or derivatives thereof. A nucleic acid may be natural or synthetic.

The terms "fluorescent nucleic acid stain" or "fluorescent nucleic acid dye" refers to a dye capable of binding to a nucleic acid to form a fluorescent dye-nucleic acid complex. A fluorescent nucleic acid dye is typically non-fluorescent or weakly fluorescent by itself, but becomes highly fluorescent upon nucleic acid binding. The term "fluorescent DNA dye" refers to a dye that becomes fluorescent upon binding to DNA.

The term "TE" refers to an aqueous buffer comprising about 10 mM Tris and about 1 mM EDTA. The term "TBE" refers to an aqueous buffer comprising about 89 mM Tris, about 89 mM borate, and about 2 mM EDTA, with a pH of about 8.3 The term "TAE" refers to an aqueous buffer comprising about 40 mM Tris, about 20 mM acetate, and about 2 mM EDTA, with a pH of about 8.1.

In some embodiments, the unsymmetrical cyanine dyes of the invention comprise: 1) a first heterocyclic ring system that is a substituted benzazolium ring, the ring system is optionally further substituted by a variety of substituents; 2) a bridging methine; and 3) a second heterocyclic ring that is a pyridinium or quinolinium ring system, one or more positions of which may be substituted by substituents. The dye structures generally have the formula:

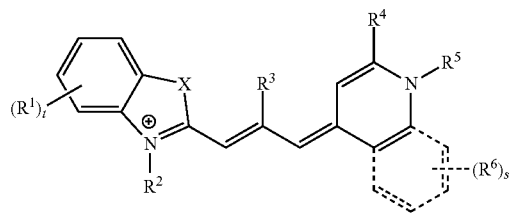

The double bond in the center can be in either cis or trans configuration. Mixtures of both configurations are also possible in a simple of a particular compound.

X can be one of O, S, or $C(CH_3)_2$. In preferred embodiments, X is O, or S.

Groups $R^1$ and $R^6$ can independently comprise or be hydrogen, carboxy, sulfo, sulfonamide, halogen, CN, or alkoxy. Preferably the substitute $R^1$ is hydrogen, carboxy, sulfo, or sulfonamide. Preferably the substitute $R^6$ is hydrogen, or methoxyl.

The value t or s can be 0, 1, 2, 3 and 4. When the substituent group $R^1$ or $R^6$ is more than one substituent, the substituents may be the same or different. Typically, the compound contains no more than one $R^1$ or $R^6$ that is not hydrogen.

The substitute $R^2$ can be an alkyl, or alkyl group substituted by a carboxy, or a sulfo. Preferably the substitute $R^2$ is an alkyl group having 1-6 carbons, more preferably methyl.

The substitute $R^3$ can be H, $C_6H_4CO_2R^7$, or $C_6H_4CH_2N(R^7)_2$, where $R^7$ is an alkyl. Incorporation of a non-hydrogen substituent $R^3$ can be used to adjust the binding selectivity on DNA or RNA.

The substitute $R^4$ can be H, alkyl, aryl, halogen, alkoxy, alkylamino, or alkylthio. Preferably the substitute $R^4$ is H, alkyl having 1-6 carbons, alkylamino, or dialkylamino.

The substitute $R^5$ can be an alkyl, aryl, alkyl group substituted by a carboxy, or a sulfo, or $-(CH_2)_a-[O-(CH_2)_b]_m-O-Z$, where Z is H, alkyl, or carboxy; each of a and b is an integer from 1 to 4; m is an integer selected from 0 to 4. Preferably the substitute $R^5$ is alkyl having 1-6 carbons, aryl, $-(CH_2)_a-[O-(CH_2)_b]_m-O-Z$, where Z is H, methyl; each of a and b is an integer from 2 to 3; m is an integer selected from 0 to 4.

In some embodiments, at least one of R', $R^2$, $R^5$ and $R^6$ comprises or is carboxy, sulfo, sulfonamide, alkyl group substituted by a carboxy, alkyl group substituted by a sulfo, or $-Y-(CH_2)_a-[O-(CH_2)_b]_m-O-Z$, where Y is absent, O, NH(C=O), C(=O)NH, or S(=O)$_2$NH; Z is H, or alkyl; each of a and b is an integer from 1 to 4; m is an integer selected from 0 to 4.

In some embodiments, at least one of $R^1$, $R^2$, $R^5$ and $R^6$ comprises or is sulfo, sulfonamide, alkyl group substituted by a carboxy, or alkyl group substituted by a sulfo.

In some embodiments, $R^1$ is H or sulfo, $R^2$ is methyl or ethyl, $R^4$ is H or alkyl, $R^6$ is H or methoxyl, and $R^5$ is alkyl having 1-6 carbons.

Certain nonlimiting exemplary unsymmetrical cyanine dyes are shown in Tables 1.

TABLE 1

Nonlimiting exemplary unsymmetrical cyanine dye structures

| Compound | Structure |
|---|---|
| 1 | 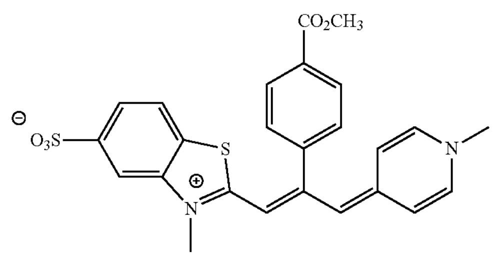 |
| 2 | 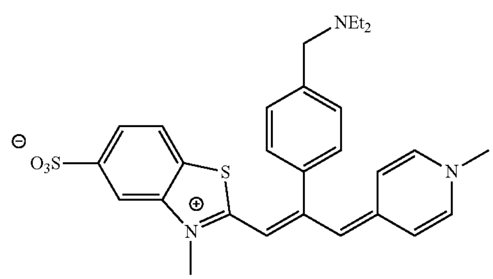 |
| 3 | 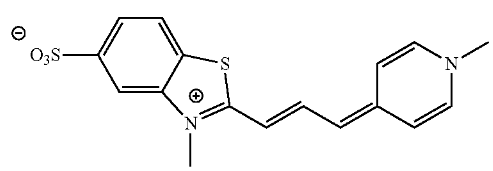 |
| 4 | 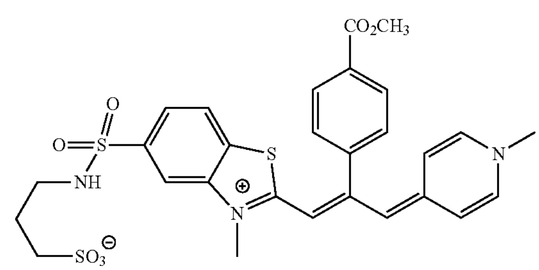 |

TABLE 1-continued
Nonlimiting exemplary unsymmetrical cyanine dye structures
| Compound | Structure |
|---|---|
| 5 | 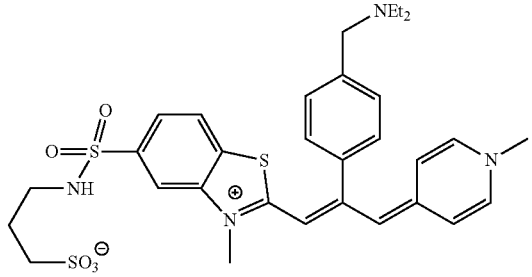 |
| 6 | 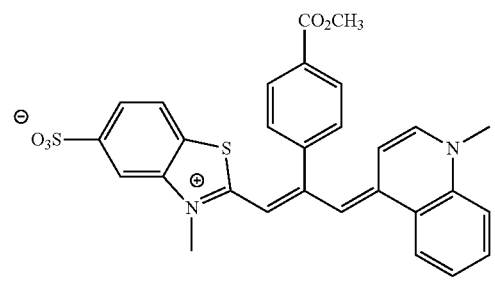 |
| 7 | 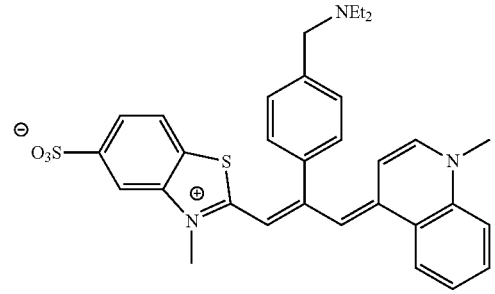 |
| 8 | 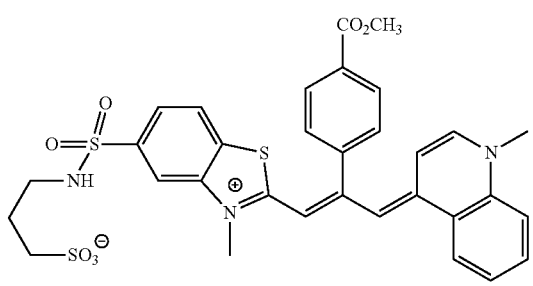 |
| 9 | 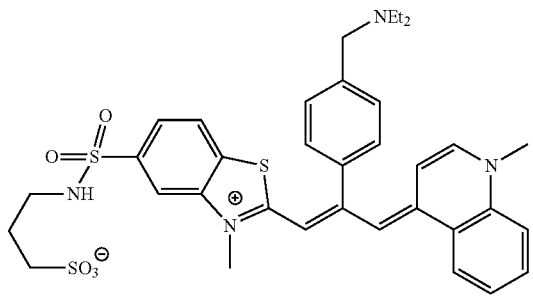 |

TABLE 1-continued
Nonlimiting exemplary unsymmetrical cyanine dye structures
| Compound | Structure |
|---|---|
| 10 | 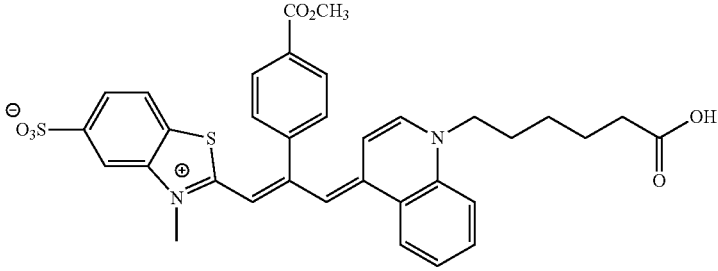 |
| 11 | 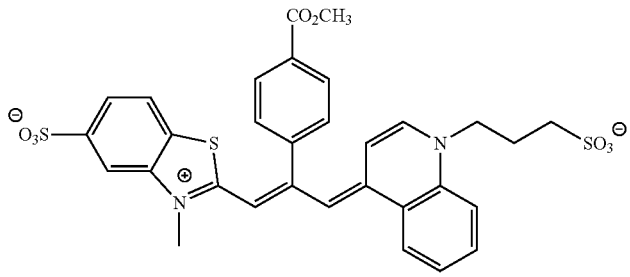 |
| 12 | 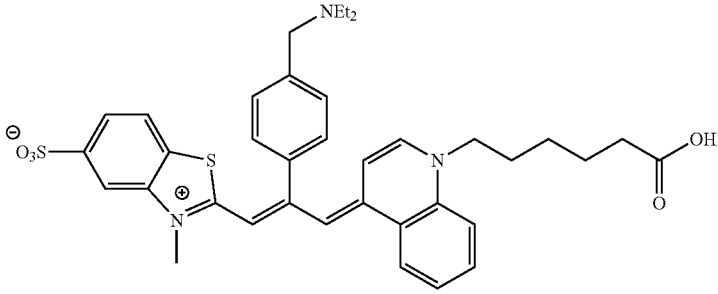 |
| 13 | 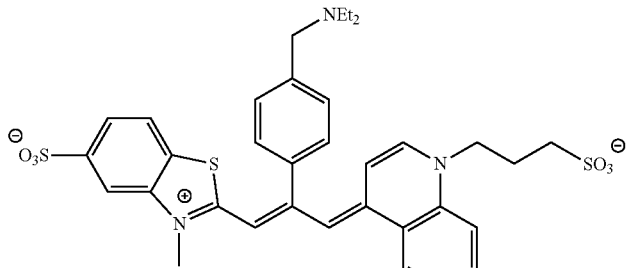 |
| 14 | 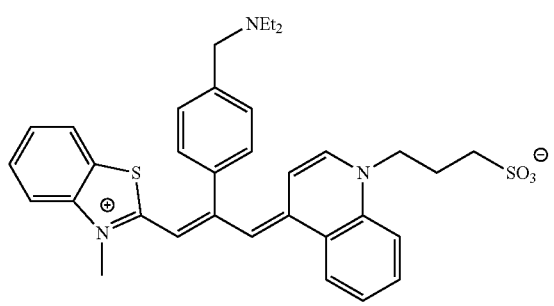 |

TABLE 1-continued
Nonlimiting exemplary unsymmetrical cyanine dye structures
| Compound | Structure |
|---|---|
| 15 | 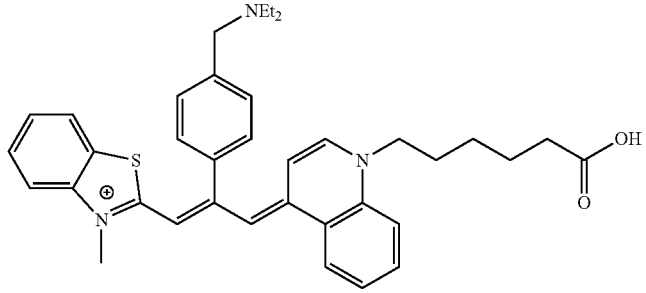 |
| 16 | 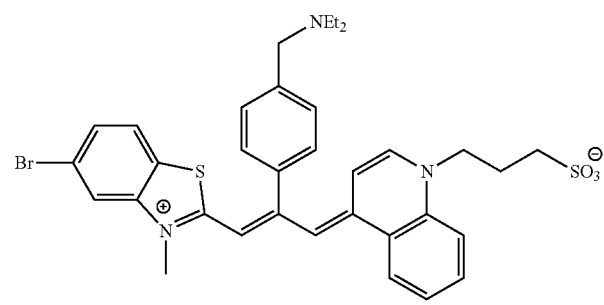 |
| 17 | 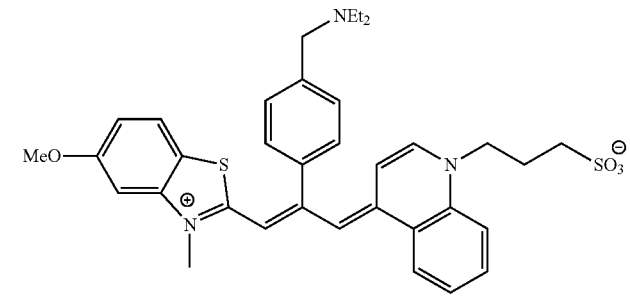 |
| 18 | 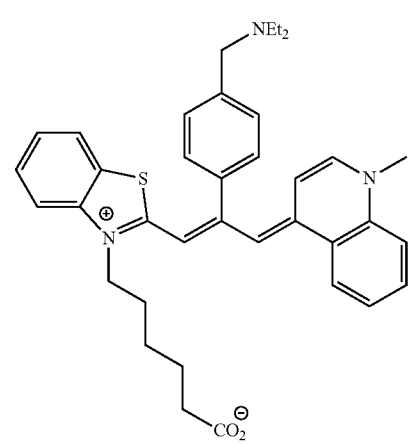 |

TABLE 1-continued

Nonlimiting exemplary unsymmetrical cyanine dye structures

| Compound | Structure |
|---|---|
| 19 | 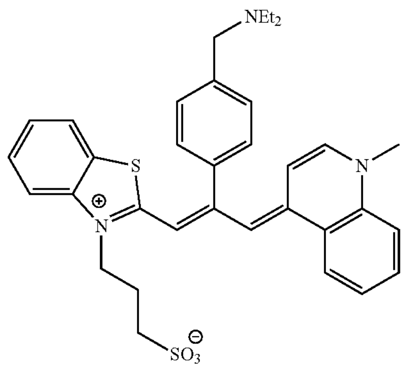 |
| 20 | 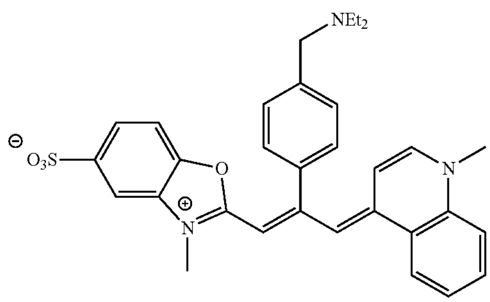 |
| 21 | 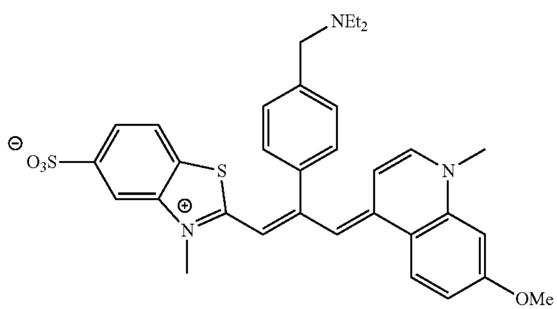 |
| 22 | 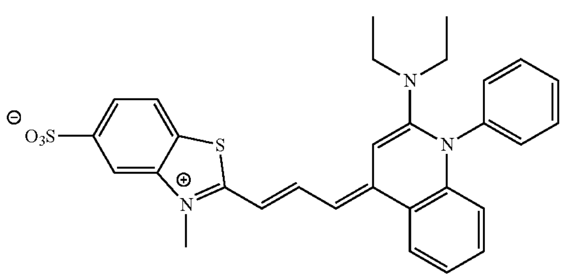 |
| 23 | 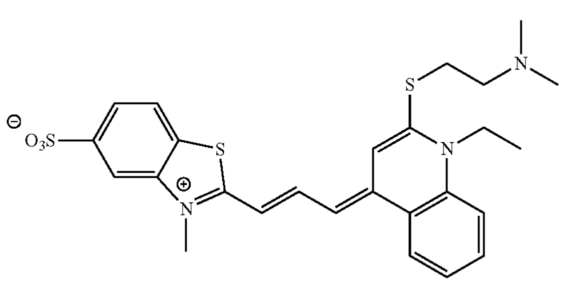 |

TABLE 1-continued

Nonlimiting exemplary unsymmetrical cyanine dye structures

| Compound | Structure |
|---|---|
| 24 | 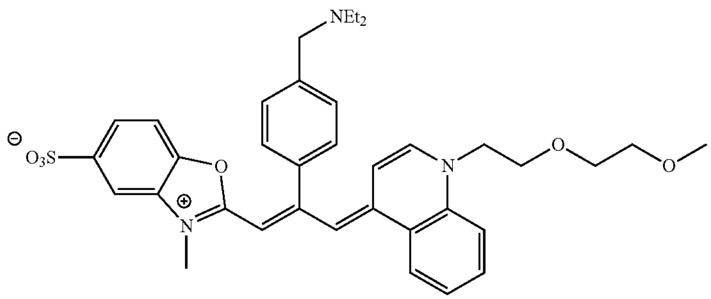 |
| 25 | 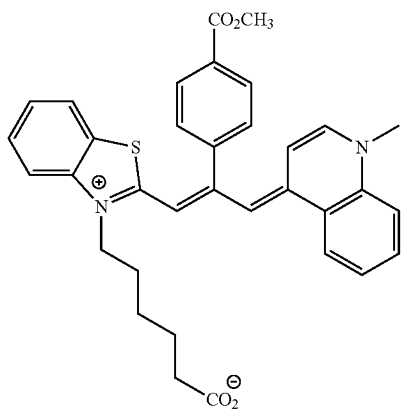 |
| 26 | 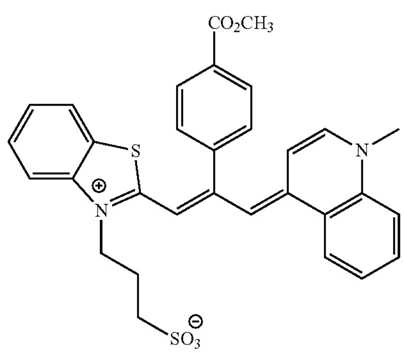 |
| 27 | 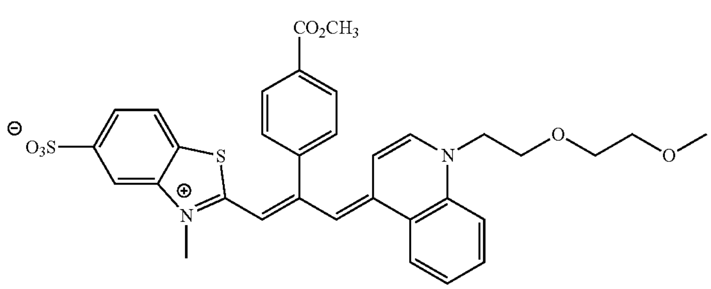 |

TABLE 1-continued

Nonlimiting exemplary unsymmetrical cyanine dye structures

| Compound | Structure |
|---|---|
| 28 | 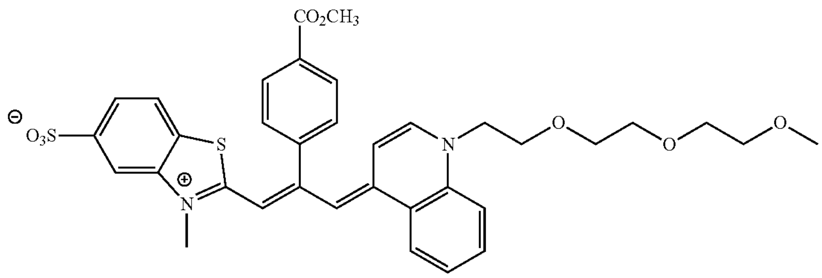 |
| 29 | 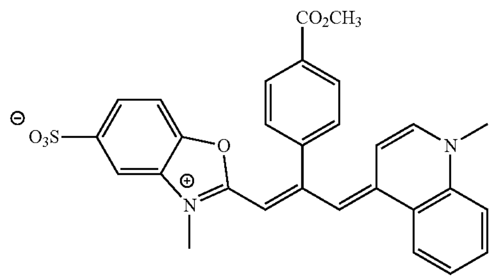 |
| 30 | 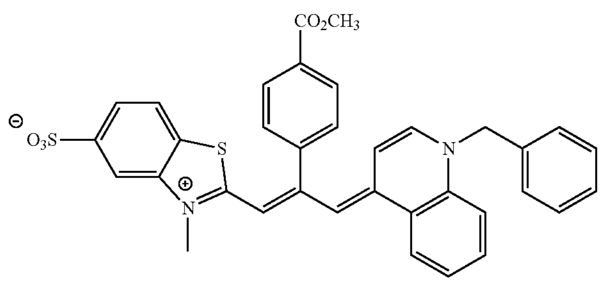 |

In some embodiments, the dyes of this invention have absorption wavelength in the range from about 500 nm to about 750 nm, however the dyes generally provide only a negligible fluorescence emission peak unless bound to nucleic acids. Upon binding with DNA or RNA, the optical properties of the dyes change significantly. The fluorescence intensity of the dyes in the bound state is generally over 100 fold brighter than unbound state. In particular, the absorption curve typically shifts to a longer wavelength. Typically, the absorption curve shift is between about 5 nm and about 20 nm. Generally, the bound dye of this invention have a Stokes shift of between about 15 nm and about 25 nm.

In some embodiments, the change of spectral properties when the dye is bound to nucleic acids can be used to quantitatively or qualitatively analysis the presence or the amount of nucleic acids in a sample. To analysis the nucleic acids in a sample, the dye in a buffered solution is added to the sample thought to contain nucleic acids. Measurement of fluorescence or absorbance of the solution before and after the combination of the sample with nucleic acids are compared. The fluorescence intensity of the nucleic acid-dye complex is proportional to the amount of nucleic acid in the sample. Alternatively, the absorbance of solutions with and without the addition of nucleic acids can be compared.

In some embodiments, the change of fluorescence intensity can be used to qualitatively measure the activity of enzymes, such as DNase or RNase that hydrolyses the nuleic acids, for example, and the changes of nucleic acids in a sample. The fluorescence of the solution containing dye and nucleic acids is compared with the fluorescence of the solution after the addition of a hydrolyzing enzyme.

In some embodiments, the dyes of this invention can be used as nucleic acid stains in cells. Because different dyes have different cell membrane permeability, the dyes with cell permeant can be used for living cell stains, and the dyes with cell impermeant can be used for dead or fixed cell stains. Besides, the dyes can be used to measure the viability of cells in the sample. Cell death or toxicity usually results in loss of cell membrane integrity. When the cell membrane is damaged, the nucleic acids inside the cell become accessible to the dyes with cell impermeant. By choosing one dye with cell permeant and another dye with cell impermeant and different emission wavelength, the live/dead cells can be differentiated based on fluorescence signals at two different emission wavelengths.

In some embodiments, the intensity of fluorescence can be used to measure the effect of a cytotoxic event including exposure to a chemical reagent, the addition of a biological agent, or other change in environmental condition that results in membrane disruption. The effect of a cytotoxic event can be observed over time, or after a fixed period of time. To measure the effect of a cytotoxic event that involves the addition of a cytotoxic reagent, a stock solution of the reagent is prepared at a concentration greater that what is expected to be a toxic dose and this is added to the cells or tissue in a suitable medium. Typically various concentrations of the reagent are added from 0 to greater than a toxic dose. Toxicity can be measured by the fluorescence intensity of cells after addition of the dyes.

In some embodiments, the dyes of this invention can be used for detection of nucleic acids immobilized relative to a matrix or a surface, or as nucleic acid gel stains. There are generally two methods for staining nucleic acids in gels using the dyes. The first method is post-gel staining, wherein a nucleic acid sample is separated by gel electrophoresis, the gel comprising the separated nucleic acids is incubated in a solution comprising the dye, the gel may be destained, if desirable or necessary to remove background fluorescence, and the resulting gel is viewed using a transilluminator or laser scanner. The second method is pre-cast gel staining, wherein a gel is premixed or pre-embedded with the dye, the nucleic acid sample is separated by electrophoresis using the pre-cast gel, and the stained gel is viewed using a transilluminator or laser scanner. In general, the dyes of this invention can be used for post-gel staining, pre-cast gel staining, or variations thereof.

In some embodiments, the dyes of this invention may be included in a kit. A kit may comprise the dye, information or a protocol regarding use of the dye or the kit, and/or other useful or necessary materials or reagents, such as any materials or reagents suitable for the detection of nucleic acids, for example, such as a buffer, a detergent, a DNA or RNA standard, a DNA or RNA ladder, and/or matrix.

EXAMPLES

The examples discussed below are intended to be purely exemplary of the invention and should not be considered to limit the invention in any way. The examples are not intended to represent that the experiments below are all or the only experiments performed.

Example 1

Preparation of Compound (31)

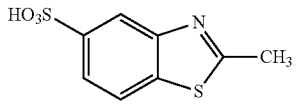

5 g of 2-Methyl benzothiazole was added dropwise to 10 mL of conc. $H_2SO_4$ at 0° C. 10 mL of fuming sulfuric acid (30% $SO_3$) was added dropwise, followed by addition of $FeCl_3$ (23 mg) at 0° C. The reaction mixture was stirred at 125° C. for 1 h. After cooling to room temperature, the mixture was added dropwise to cold acetone (~80 mL) with stirring. The resulting white precipitate was collected by filtration, and crystallized in MeOH/Ethyl acetate to give compound 31.

Example 2

Preparation of Compound (32)

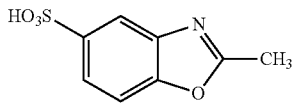

Compound 32 was prepared in a method analogous to that of compound 31, above.

Example 3

Preparation of Compound (33)

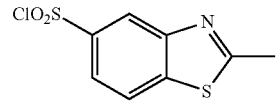

5 g of compound 31 was added in small portions to 20 mL of $POCl_3$ at 0° C. After addition, the reaction mixture was stirred at 55° C. until TLC shows the reaction is complete. After cooling to room temperature, the mixture was added dropwise to ice/water with stirring. The resulting precipitate was collected by filtration, and washed with water, and dried under high vacuum to give compound 33.

Example 4

Preparation of Compound (34)

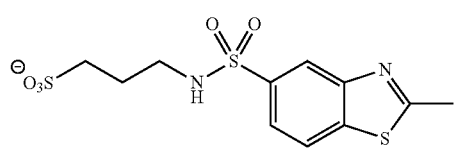

1 g (4 mmol) of compound 33 was dissolved in 5 mL DMF ° C. 835 mg (6 mmol) of 3-aminopropanesulfonic acid was added, followed by addition of triethylamine (1.4 mL, 10 mmol). The reaction mixture was stirred at room temperature until TLC shows the reaction is complete. Ethyl acetate (40 mL) was added to the stirring mixture. The resulting precipitate was collected by filtration, and washed with ethyl acetate, and dried under high vacuum to give compound 34.

Example 5

Preparation of Compound (35)

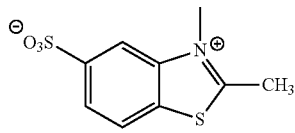

5 mmol of compound 31 and 15 mmol of methyl p-toluenesulfonate in 10 mL chlorobenzene were heated at 120° C. overnight. Then 20 mL ethyl acetate was added, and resulting mixture was refluxed for 30 min. The compound 35 was recovered by filtration as a white solid.

Example 6

Preparation of Compound (36)

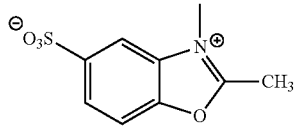

Compound 36 was prepared in a method analogous to that of compound 35, above.

Example 7

Preparation of Compound (37)

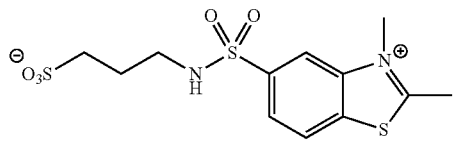

Compound 37 was prepared in a method analogous to that of compound 35, above.

Example 8

Preparation of Compound (38)

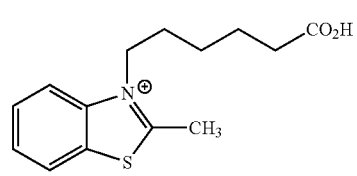 [SMILES: Cc1sc2ccccc2[n+]1CCCCCC(=O)O]

2 g of 2-Methyl benzothiazole and 7.8 g of 6-bromo-hexanoic acid in 20 mL chlorobenzene was heated at 120° C. for 48 h. Then 30 mL ethyl acetate was added, and resulting mixture was refluxed for 30 min. The supernatant was decanted and the residue was dried to give compound 38.

Example 9

Preparation of Compound (39)

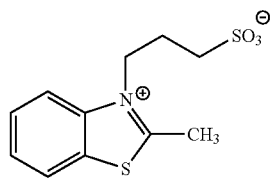

2 g of 2-Methyl benzothiazole and 5 g of 1,3-propane-sultone in 20 mL chlorobenzene was heated at 120° C. overnight. Then 30 mL ethyl acetate was added, and resulting mixture was refluxed for 30 min. The supernatant was decanted and the residue was dried to give compound 38.

Example 10

Preparation of Compound (40)

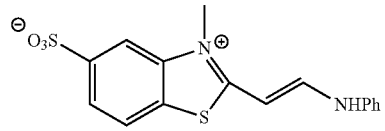

5 g of compound 35 (20.6 mmol), and 4.4 g of N,N'-diphenylformamidine (22.6 mmol) were dissolved in 10 mL acetic acid. 2.1 g of acetic anhydride (20.6 mmol) was added, and the reaction mixture was refluxed for 1 h. Then, 50 mL of ethyl acetate was added to the stirring mixture. The yellow precipitate was collected by filtration, and washed with ethyl acetate to give compound 40.

Example 11

Preparation of Compound (41)

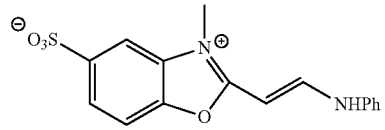

Compound 41 was prepared in a method analogous to that of compound 40, above.

Example 12

Preparation of Compound (42)

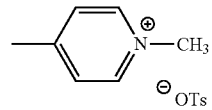

5 g of 4-Methylpyridine and 20 g of methyl p-toluene-sulfonate in 20 mL chlorobenzene was heated at 120° C. overnight. Then 30 mL ethyl acetate was added, and resulting mixture was refluxed for 30 min. The compound 42 was recovered by filtration as a white solid.

Example 13

Preparation of Compound (43)

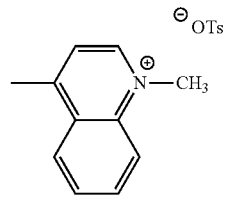

5 g of Lepidine and 10 g of methyl p-toluenesulfonate in 20 mL chlorobenzene was heated at 120° C. overnight. Then

Example 14

Preparation of Compound (44)

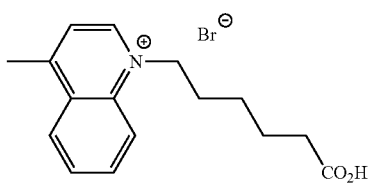 [SMILES: Cc1cc[n+](CCCCCC(=O)O)c2ccccc12 ; [Br-]]

2 g of Lepidine and 8.2 g of 6-bromohexanoic acid in 20 mL chlorobenzene was heated at 120° C. for 48 h. Then 30 mL ethyl acetate was added, and resulting mixture was refluxed for 30 min. The supernatant was decanted and the residue was dried to give compound 44.

Example 15

Preparation of Compound (45)

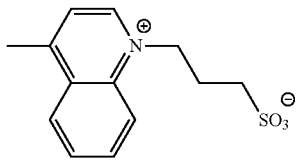

2 g of Lepidine and 5.1 g of 1,3-propanesultone in 20 mL chlorobenzene was heated at 120° C. overnight. Then 30 mL ethyl acetate was added, and resulting mixture was refluxed for 30 min. The supernatant was decanted and the residue was dried to give compound 45.

Example 16

Preparation of Compound (46)

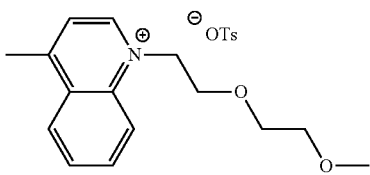

2 g of Lepidine and 12 g of 2-(2-methoxyethoxy)ethyl 4-methylbenzene-sulfonate in 20 mL chlorobenzene was heated at 120° C. overnight. Then 30 mL ethyl acetate was added, and resulting mixture was refluxed for 30 min. The supernatant was decanted and the residue was dried to give compound 46.

Example 17

Preparation of Compound (47)

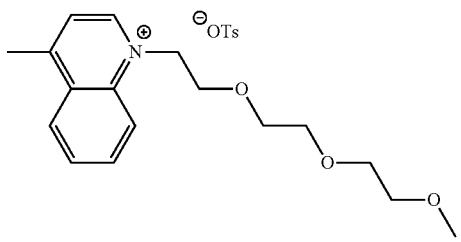

Compound 47 was prepared in a method analogous to that of compound 46, above.

Example 18

Preparation of Compound (48)

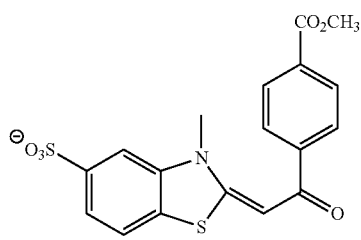

Compound 35 (5 mmol) and methyl 4-(chlorocarbonyl)benzoate (5 mmol) were dissolved in 15 mL dry pyridine. The reaction mixture was stirred at 45° C. overnight. The reaction mixture was concentrate, and the crude was purified by $SiO_2$ column to give compound 48.

Example 19

Preparation of Compounds (49)

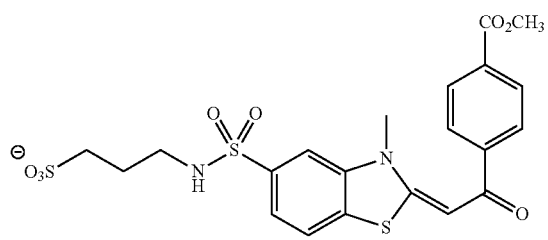

Compound 49 was prepared in a method analogous to that of compound 48, above.

Example 20

Preparation of Compound (50)

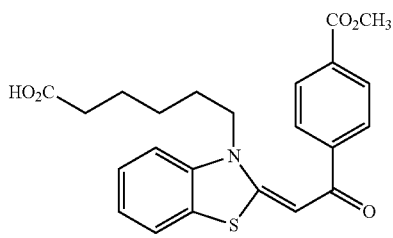 [SMILES: COC(=O)c1ccc(C(=O)/C=C2/Sc3ccccc3N2CCCCCC(=O)O)cc1]

Compound 50 was prepared in a method analogous to that of compound 48, above.

Example 21

Preparation of Compound (51)

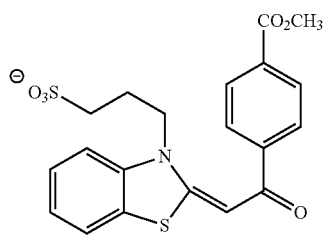

Compound 51 was prepared in a method analogous to that of compound 48, above.

Example 22

Preparation of Compound (52)

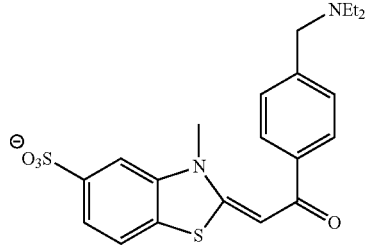

Compound 35 (5 mmol) and 4-((diethylamino)methyl) benzoyl chloride (5 mmol) were dissolved in 15 mL dry pyridine. The reaction mixture was stirred at 45° C. overnight. The reaction mixture was concentrate, and the crude was purified by $SiO_2$ column to give compound 52.

Example 23

Preparation of Compound (53)

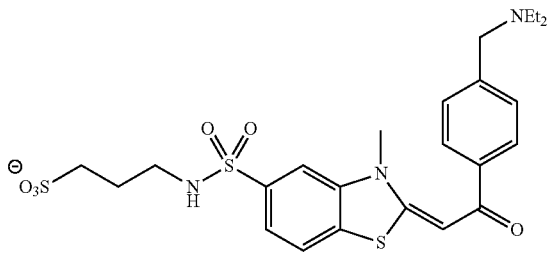

Compound 53 was prepared in a method analogous to that of compound 52, above.

Example 24

Preparation of Compound (54)

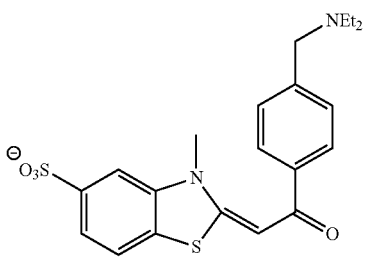

Compound 54 was prepared in a method analogous to that of compound 52, above.

Example 25

Preparation of Compound (1)

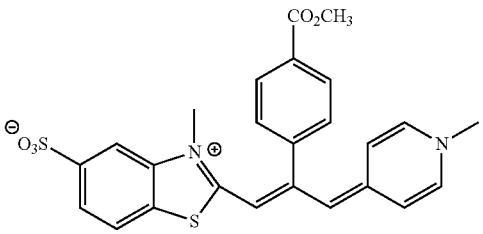

Compound 48 (1 mmol) was dissolved in 6 mL 1,2-dichloroethane, $POCl_3$ (1 mL) was added. The reaction mixture was refluxed for 2 h, then the mixture was concentrated. The residue was stirred in 30 ml ethyl aceate for 30 min, then decanted. Dissolve the residue in dichloromethane (10 mL), then add compound 42 (1 mmol) and triethylamine (1 mL). The reaction mixture was stirred at room temperature for 2 h. Then, the mixture was concentrated, and purified by reverse phase HPLC to give compound 1.

Example 26

Preparation of Compound (2)

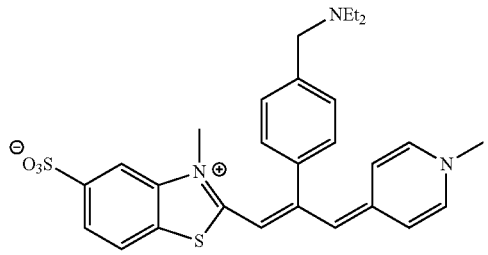

Compound 2 was prepared in a method analogous to that of compound 1, above.

Example 27

Preparation of Compound (3)

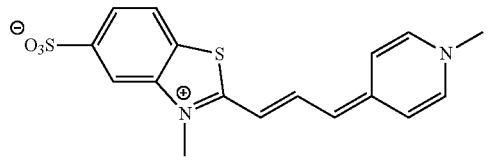

Compound 40 (1 mmol) and compound 42 (1 mmol) were suspended in 5 mL dichloromethane. Triethylamine (3 mmol) and acetic anhydride (1 mmol) were added, and the reaction mixture was stirred ar room temperature for 2 hours. Then, ethyl acetate (20 mL) was added to the stirring mixture, and the blue solid was collected by filtration. Then the solid was triturated in ethyl acetate, acetone, and acetonitrile. The blue solid was collected by filtration and dried in vacuo to give compound 3.

Example 28

Preparation of Compound (4)

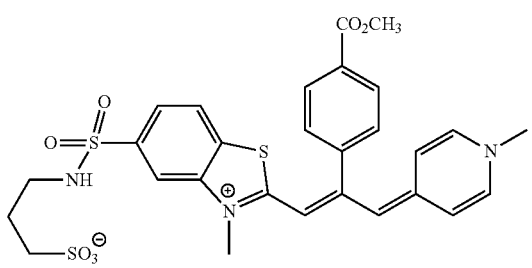

Compound 4 was prepared in a method analogous to that of compound 1, above.

Example 29

Preparation of Compound (5)

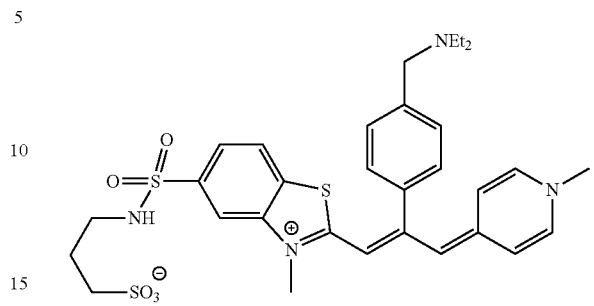

Compound 5 was prepared in a method analogous to that of compound 1, above.

Example 30

Preparation of Compound (6)

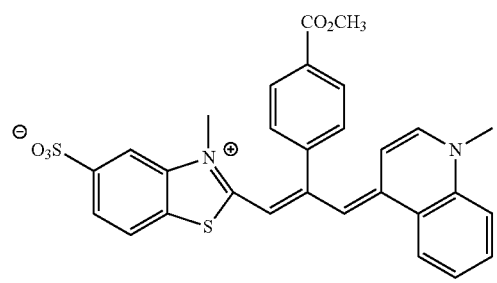

Compound 48 (1 mmol) was dissolved in 6 mL 1,2-dichloroethane, POCl$_3$ (1 mL) was added. The reaction mixture was refluxed for 2 h, then the mixture was concentrated. The residue was stirred in 30 ml ethyl aceate for 30 min, then decanted. Dissolve the residue in dichloromethane (10 mL), then add compound 43 (1 mmol) and triethylamine (1 mL). The reaction mixture was stirred at room temperature for 2 h. Then, the mixture was concentrated, and purified by reverse phase HPLC to give compound 6.

Example 31

Preparation of Compound (7)

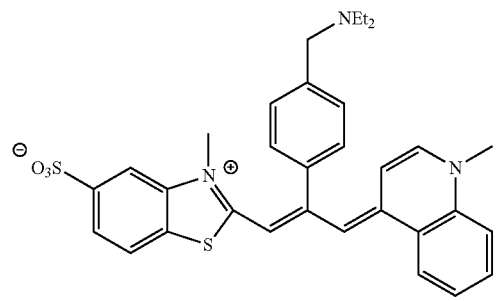

Compound 7 was prepared in a method analogous to that of compound 6, above.

Example 32

Preparation of Compound (8)

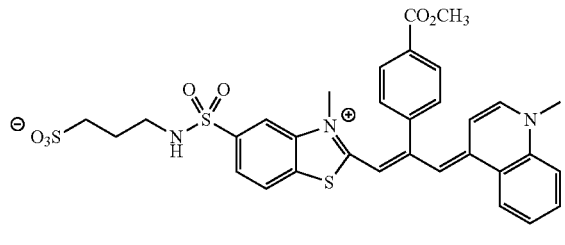

Compound 8 was prepared in a method analogous to that of compound 6, above.

Example 33

Preparation of Compound (9)

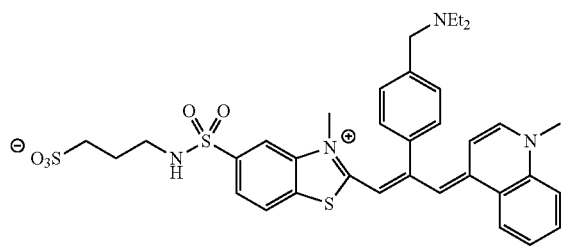

Compound 9 was prepared in a method analogous to that of compound 6, above.

Example 34

Preparation of Compound (10)

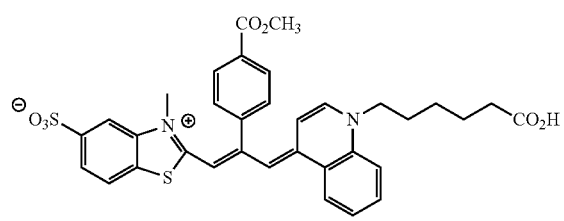

Compound 48 (1 mmol) was dissolved in 6 mL 1,2-dichloroethane, $POCl_3$ (1 mL) was added. The reaction mixture was refluxed for 2 h, then the mixture was concentrated. The residue was stirred in 30 ml ethyl aceate for 30 min, then decanted. Dissolve the residue in dichloromethane (10 mL), then add compound 44 (1 mmol) and triethylamine (1 mL). The reaction mixture was stirred at room temperature for 2 h. Then, the mixture was concentrated, and purified by reverse phase HPLC to give compound 10.

Example 35

Preparation of Compound (11)

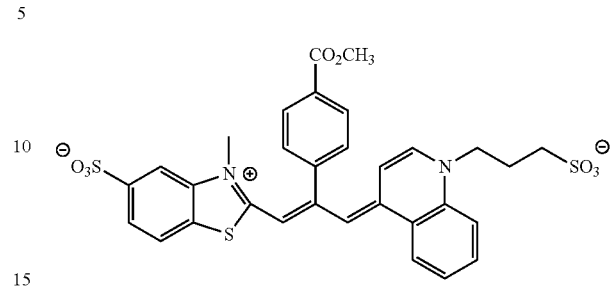

Compound 48 (1 mmol) was dissolved in 6 mL 1,2-dichloroethane, $POCl_3$ (1 mL) was added. The reaction mixture was refluxed for 2 h, then the mixture was concentrated. The residue was stirred in 30 ml ethyl aceate for 30 min, then decanted. Dissolve the residue in dichloromethane (10 mL), then add compound 45 (1 mmol) and triethylamine (1 mL). The reaction mixture was stirred at room temperature for 2 h. Then, the mixture was concentrated, and purified by reverse phase HPLC to give compound 11.

Example 36

Preparation of Compound (12)

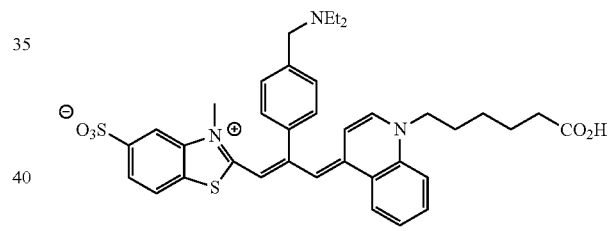

Compound 12 was prepared in a method analogous to that of compound 10, above.

Example 37

Preparation of Compound (13)

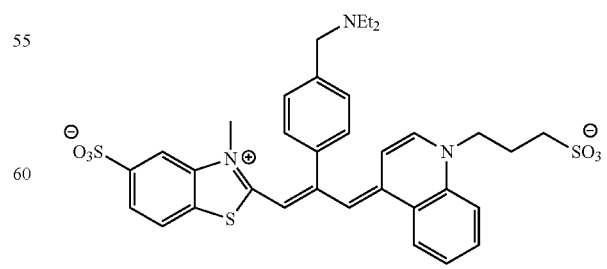

Compound 13 was prepared in a method analogous to that of compound 11, above.

Example 38

Preparation of Compound (14)

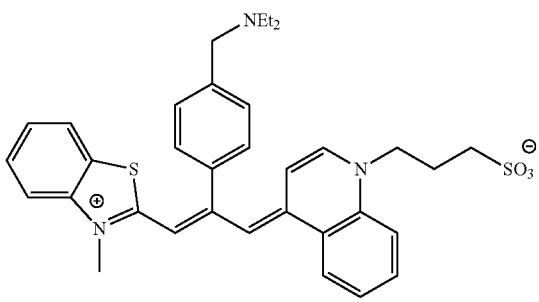

Compound 14 was prepared in a method analogous to that of compound 11, above.

Example 39

Preparation of Compound (15)

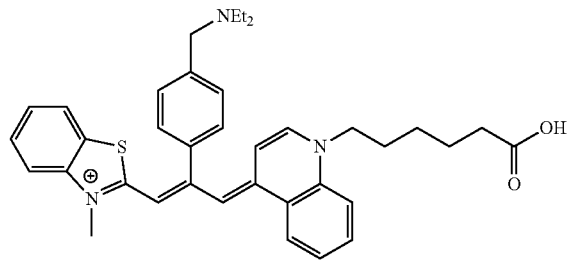

Compound 15 was prepared in a method analogous to that of compound 10, above.

Example 40

Preparation of Compound (24)

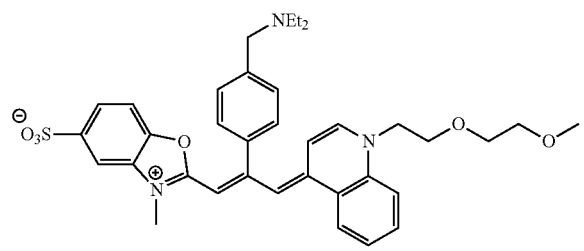

Compound 54 (1 mmol) was dissolved in 6 mL 1,2-dichloroethane, $POCl_3$ (1 mL) was added. The reaction mixture was refluxed for 2 h, then the mixture was concentrated. The residue was stirred in 30 ml ethyl aceate for 30 min, then decanted. Dissolve the residue in dichloromethane (10 mL), then add compound 46 (1 mmol) and triethylamine (1 mL). The reaction mixture was stirred at room temperature for 2 h. Then, the mixture was concentrated, and purified by reverse phase HPLC to give compound 24.

Example 41

Preparation of Compound (27)

Compound 48 (1 mmol) was dissolved in 6 mL 1,2-dichloroethane, $POCl_3$ (1 mL) was added. The reaction mixture was refluxed for 2 h, then the mixture was concentrated. The residue was stirred in 30 ml ethyl aceate for 30 min, then decanted. Dissolve the residue in dichloromethane (10 mL), then add compound 46 (1 mmol) and triethylamine (1 mL). The reaction mixture was stirred at room temperature for 2 h. Then, the mixture was concentrated, and purified by reverse phase HPLC to give compound 24.

Example 42

Preparation of Compound (28)

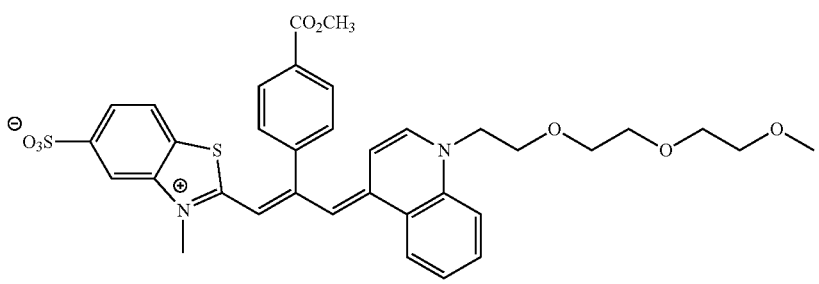

Compound 28 was prepared in a method analogous to that of compound 27, above.

Example 43

Selectivity Test on RNA vs dsDNA

A stock solution of compound 9 was prepared at 100 µM concentration in DMSO. Calf thymus DNA, and E. coli rRNA were prepared at 10 µg/mL concentration in 1×TE buffer, individually. To 1 mL of DNA solution and 1 mL of RNA solution was added with 5 µL of compound 9, individually. The emission spectrum associated with each of the solutions was scaned at excitation wavelength 620 nm. A graphical representation of emission spectra is shown in FIG. 1. As shown, compound 9 has good selectivity for RNA versus DNA.

Example 44

Selectivity Test on a Mixture of RNA and DNA

A series of RNA and DNA dilutions up to 1000 ng/mL in 1×TE buffer is added to the wells of a 96-well microplate. A series of mixture of RNA and DNA is prepared according to the following table, and is added to separate wells.

| RNA (ng/mL) | DNA (ng/mL) |
|---|---|
| 0 | 1000 |
| 50 | 950 |
| 100 | 900 |
| 200 | 800 |
| 400 | 600 |
| 600 | 400 |
| 800 | 200 |
| 1000 | 0 |

Figure 2:
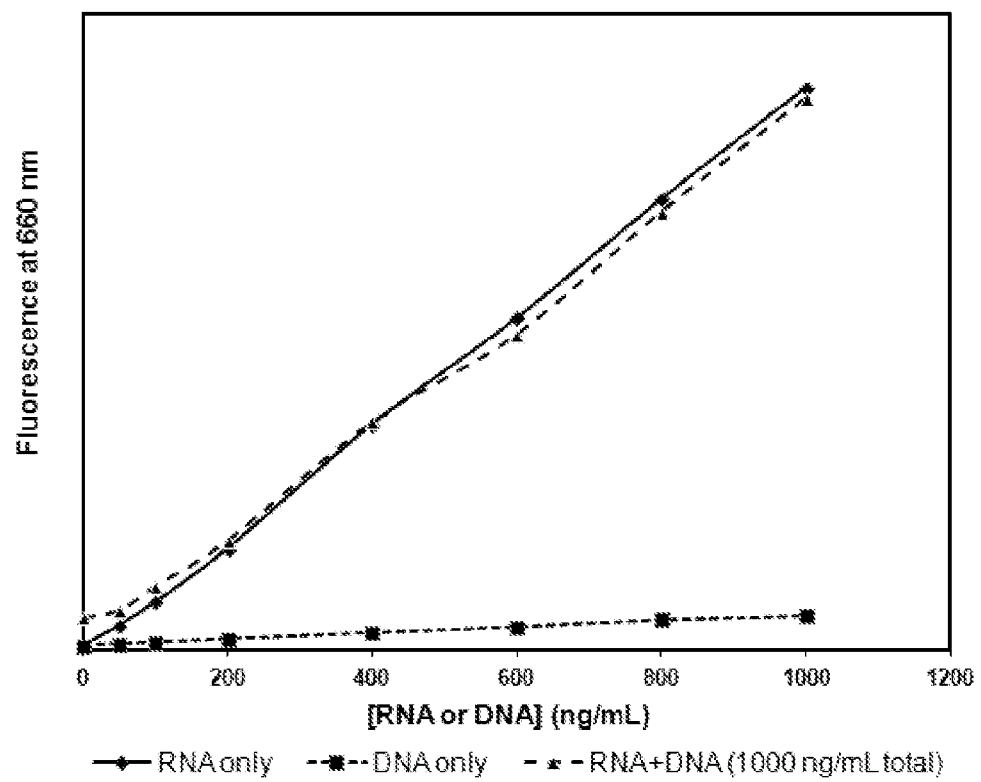
FIG. 2 shows a plot of the fluorescence intensity of compound 79 in the presence of rRNA, calf thymus DNA and a mixture of RNA and DNA in solution, respectively.

Compound 9 is added to each well at a final concentration of 400 nM. The fluorescence intensity is measured on a fluorescence plate reader with Ex/Em=620/660 nm. The results are shown in FIG. 2. As shown, the fluorescence intensity of compound 9 has nice linear response with RNA concentration, but little to no signal with DNA alone. The results also show the fluorescence intensity of mixture of RNA and DNA is the same for the corresponding concentration of RNA.

In another experiment, a series of RNA and DNA dilutions up to 200 ng/mL in 1×TE buffer is added to the wells of a 96-well microplate. A series of mixture of RNA and DNA at 1:1 ratio is prepared according to the following table, and is added to separate wells.

| RNA (ng/mL) | DNA (ng/mL) |
|---|---|
| 0 | 0 |
| 10 | 10 |
| 20 | 20 |
| 40 | 40 |
| 80 | 80 |
| 125 | 125 |
| 160 | 160 |
| 200 | 200 |

Figure 3:
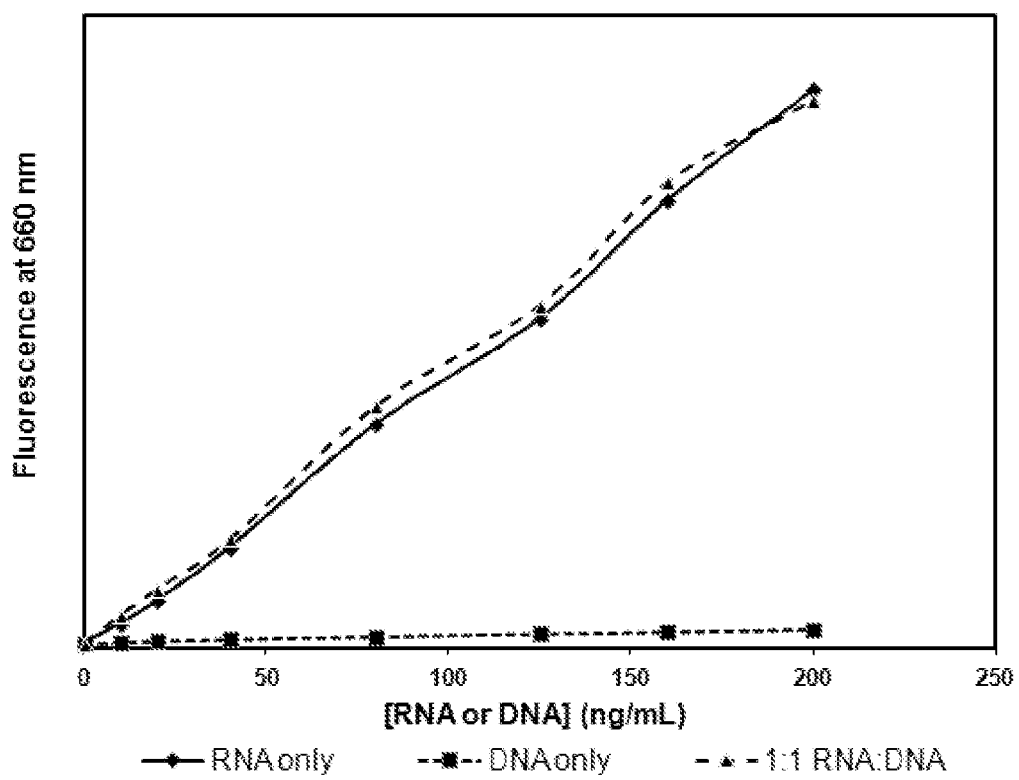
FIG. 3 shows a plot of the fluorescence intensity of compound 9 in the presence of rRNA, calf thymus DNA and a mixture of RNA and DNA in solution, respectively.

Compound 9 is added to each well at a final concentration of 100 nM. The fluorescence intensity is measured on a fluorescence plate reader with Ex/Em=620/660 nm. The results are shown in FIG. 3. As shown, compound 9 has excellent selectivity on RNA on a mixture of RNA and DNA.

Example 45

Selectivity Test on Different Source of RNA

Figure 4:
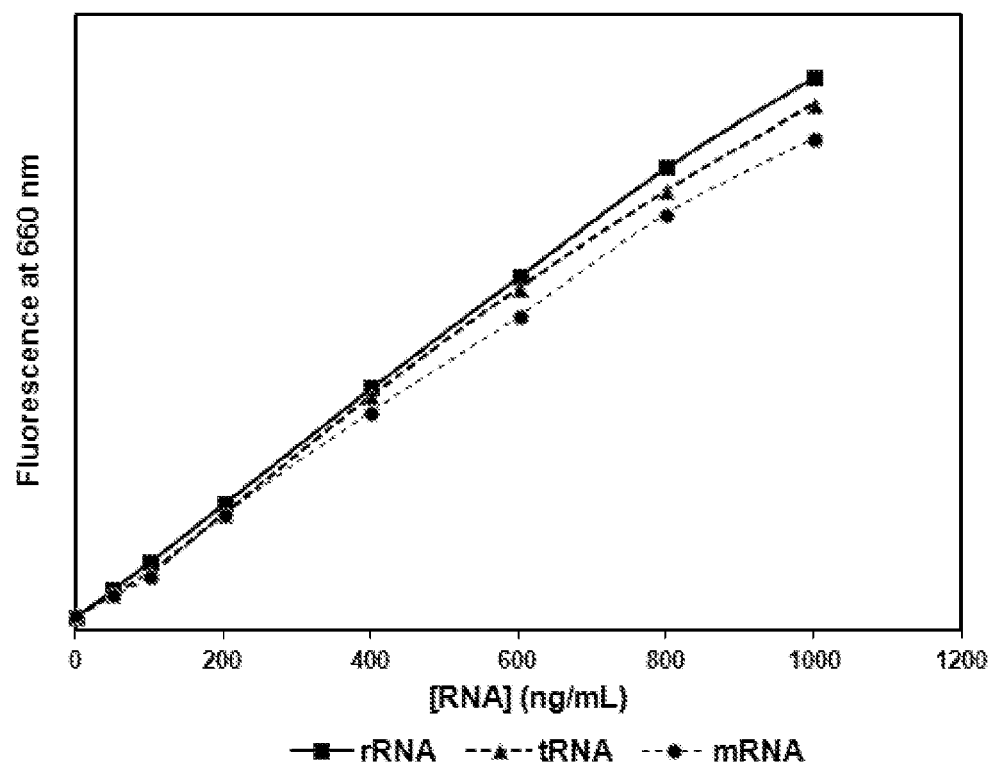
FIG. 4 shows a plot of the fluorescence intensity of compound 9 when associated with rRNA, tRNA and mRNA in solution, respectively.

A series of rRNA, tRNA and mRNA dilutions up to 1000 ng/mL in 1×TE buffer is added to the wells of a 96-well microplate. Compound 9 is added to each well at a final concentration of 400 nM. The fluorescence intensity is measured on a fluorescence plate reader with Ex/Em=620/660 nm. The results are shown in FIG. 4. As shown, compound 9 exhibits comparable fluorescent signal when associated with each varity of RNA tested.

Example 46

Comparsion Study of Quantitation of RNA in Solution

Figure 5:
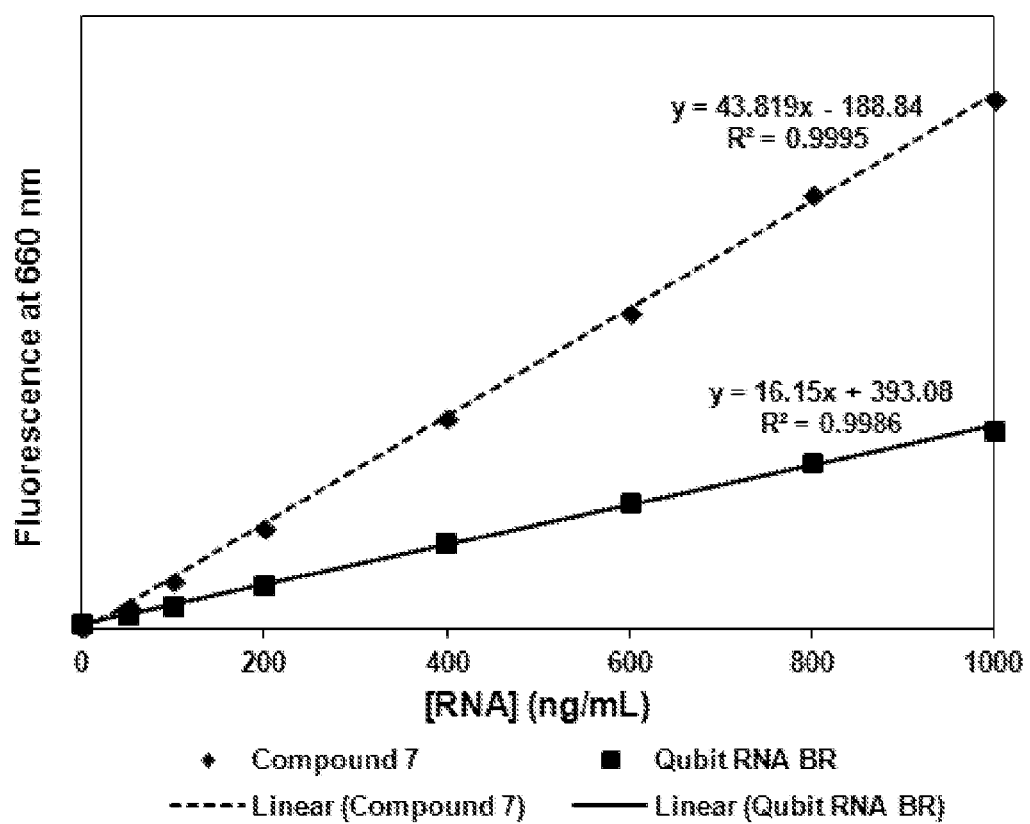
FIG. 5 shows a plot of the fluorescence intensity of compound 7 and Qubit RNA BR reagent when associated with rRNA respectively, in increasing concentrations of the RNA.

A series of rRNA dilutions up to 1000 ng/mL in 1×TE buffer is added to the wells of a 96-well microplate. Compound 7 and Qubit RNA BR reagent from Life Technologies are added to each well, respectively. The fluorescence intensity is measured on a fluorescence plate reader with Ex/Em=620/660 nm. The results are shown in FIG. 5. As shown, compound 7 exhibits better sensitivity than Qubit RNA BR reagent.

Example 47

Detection of Nucleic Acids in Electrophoretic Gels

Agarose gels (1% agarose) are prepared according to a standard protocol. Serial two-fold dilutions of 1 kb DNA Ladder from Invitrogen and rRNA from Roche are prepared, and the resulting DNA and RNA samples are loaded onto an agarose gel. The DNA and RNA samples are electrophoretically separated in 1×TBE buffer using a standard protocol. A stock solution of compound 9 is diluted into ~1 µM final concentration in 1×TE buffer. The agarose gels are incubated in the staining solutions for ~30 min to stain the gels. The stained nucleic acid bands are recorded using Fuji FLA-3000 gel scanner, using 633 nm laser illumination, and a 675 nm filter. The results show the RNA bands exhibit much brighter fluorescence signal than the corresponding DNA bands.

Example 48

Detection of Nucleic Acids on Microarrays

A microarray consisting of a dilution series of DNA marker and rRNA is printed on a slide using a microarray spotter. The slide is equilibrated in 1×SSC buffer to remove any excess printing buffer, and then soaked with compound 9 solution at ~1 µM final concentration in 1×TE buffer for 5 minutes, followed by a 5 minute wash in 1×TE buffer to remove any excess compound. The slide is then imaged using a array scaner using 633 nm laser excitation. The resulting image clearly shows the rRNA spots are stained by the dye, while the DNA spots remained undetectable.

The invention claimed is:

1. A compound having the formula:

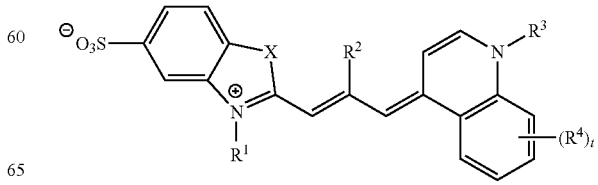

wherein:

X is O, S, or C(CH$_3$)$_2$;

R$^1$ is an alkyl, or alkyl group substituted by a carboxy, or a sulfo;

R$^2$ is H, C$_6$H$_4$CO$_2$CH$_3$, or C$_6$H$_4$CH$_2$N(CH$_2$CH$_3$)$_2$;

R$^3$ is an alkyl, or alkyl group substituted by a carboxy, a sulfo, or —(CH$_2$)$_a$—[O—(CH$_2$)$_b$]$_m$—O—Z, where Z is H, or alkyl; each of a and b is an integer from 1 to 4; m is an integer selected from 0 to 4;

R$^4$ is independently hydrogen, halogen, CN, or alkoxy;

t is an integer from 0 to 4.

2. The compound according to claim 1, wherein X is O, or S.

3. The compound according to claim 2, wherein R$^1$ is methyl, or ethyl.

4. The compound according to claim 3, wherein R$^2$ is C$_6$H$_4$CO$_2$CH$_3$, or C$_6$H$_4$CH$_2$N(CH$_2$CH$_3$)$_2$.

5. The compound according to claim 4, wherein R$^3$ is alkyl.

6. The compound according to claim 5, wherein R$^4$ is H, methoxy, Br, Cl, or F.

7. The compound according to claim 6, wherein X is S, R$^1$ is methyl, R$^2$ is C$_6$H$_4$CO$_2$CH$_3$, or C$_6$H$_4$CH$_2$N(CH$_2$CH$_3$)$_2$, R$^3$ is methyl, and R$^4$ is H.

8. A composition comprising a nucleic acid reporter compound and a sample, wherein the nucleic acid reporter compound has the formula according to claim 1.

9. A composition according to claim 8, wherein the sample comprises biological fluids, fixed cells, tissue sections, or nucleic acid molecule.

10. A composition according to claim 9, wherein the nucleic acid molecule is RNA.

11. A kit for detecting nucletic acid in a sample, wherein the kit comprises a nucleic acid reporter compound that has the formula according to claim 1.

12. The kit according to claim 11, further comprising instructions for detecting and quantitating RNA in solution.

13. The kit according to claim 11, further comprising detection reagent, dilution buffer, or nucleic acid control.

* * * * *